(12) United States Patent
Nyfors

(10) Patent No.: US 6,826,964 B2
(45) Date of Patent: Dec. 7, 2004

(54) METHOD FOR MEASURING PROPERTIES OF FLOWING FLUIDS, AND A METERING DEVICE AND A SENSOR USED FOR PERFORMING THIS METHOD

(75) Inventor: Gustaf Ebbe Nyfors, Sandnes (NO)

(73) Assignee: Roxar ASA, Stavanger (NO)

( * ) Notice: Subject to any disclaimer, the term of this patent is extended or adjusted under 35 U.S.C. 154(b) by 29 days.

(21) Appl. No.: 10/276,175

(22) PCT Filed: May 11, 2001

(86) PCT No.: PCT/NO01/00200

§ 371 (c)(1),
(2), (4) Date: Dec. 19, 2002

(87) PCT Pub. No.: WO01/88513

PCT Pub. Date: Nov. 22, 2001

(65) Prior Publication Data

US 2004/0085077 A1 May 6, 2004

(30) Foreign Application Priority Data

May 15, 2000 (NO) .......................................... 20002511

(51) Int. Cl.$^7$ ................................................ G01F 1/74
(52) U.S. Cl. .................................................. 73/861.04
(58) Field of Search ............................ 73/861, 861.02, 73/861.04, 861.08; 324/324

(56) References Cited

U.S. PATENT DOCUMENTS

| | | | |
|---|---|---|---|
| 4,996,490 A | | 2/1991 | Scott et al. |
| 5,453,693 A | * | 9/1995 | Sinclair et al. ............. 324/324 |
| 5,754,055 A | | 5/1998 | McAdoo et al. |
| 5,926,024 A | | 7/1999 | Blount et al. |
| 6,655,221 B1 | * | 12/2003 | Aspelund et al. ........ 73/861.04 |

FOREIGN PATENT DOCUMENTS

| | | |
|---|---|---|
| GB | 2 271 637 A | 4/1994 |
| GB | 2 300 483 A | 11/1996 |
| WO | WO 99/63331 A2 | 12/1999 |
| WO | WO 01/88513 A1 | 11/2001 |

* cited by examiner

*Primary Examiner*—Edward Lefkowitz
*Assistant Examiner*—Corey D. Mack
(74) *Attorney, Agent, or Firm*—Rothwell, Figg, Ernst & Manbeck

(57) ABSTRACT

A method for measuring properties of a flowing fluid composition comprising at least two different components, while the fluid composition is flowing through a duct or channel, which flow meter comprises: at least one sensor (2, 3) in the shape of a cavity resonator through which at least a portion of the fluid composition passes; at least one electronic circuit (4) comprising a transmitting means (11) adapted to transmit an electronic signal (9) into the flowing fluid via a probe (7, 11); at least one receiving means adapted to receive a signal which has traveled through the flowing fluid composition; and at least one signal processing unit (12) adapted to deduce fluid specific signals from the received signals. An oscillator included in the electronic unit (4) may, in a preferred embodiment, be phase locked to the resonant frequency of the sensor (2, 3) (in a so-called FSA (feedback self-oscillating amplification) method). The frequency is then counted downhole and the result is transferred to the surface as a digital number for each measurement of the desired properties. The invention also relates to a meter design and to a sensor device designed to fit into the narrow annulus of a subsurface production well.

9 Claims, 3 Drawing Sheets

Figure 4:
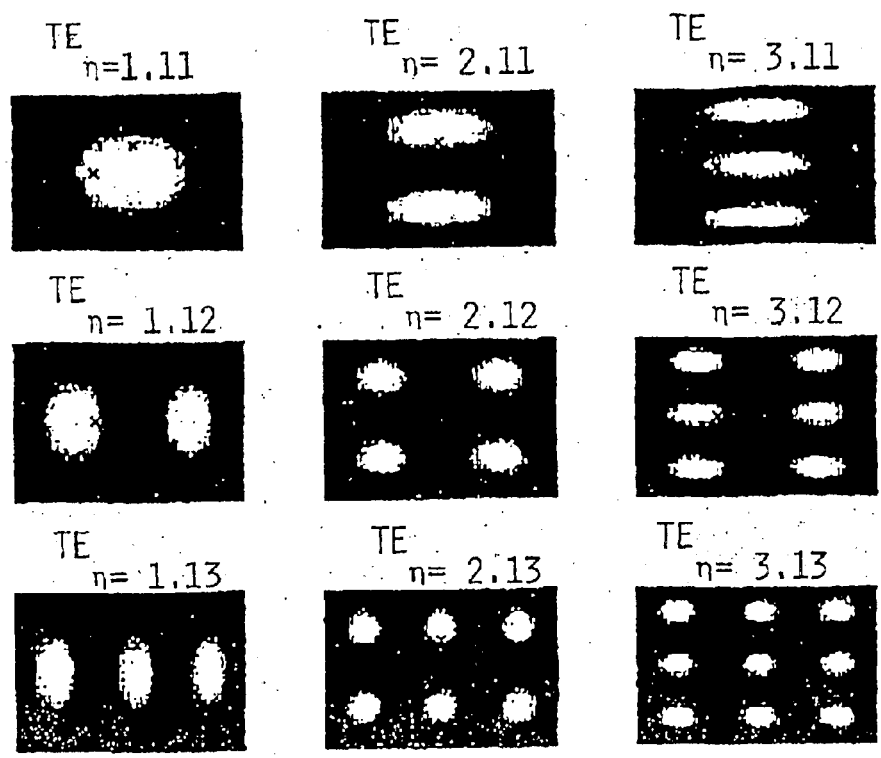

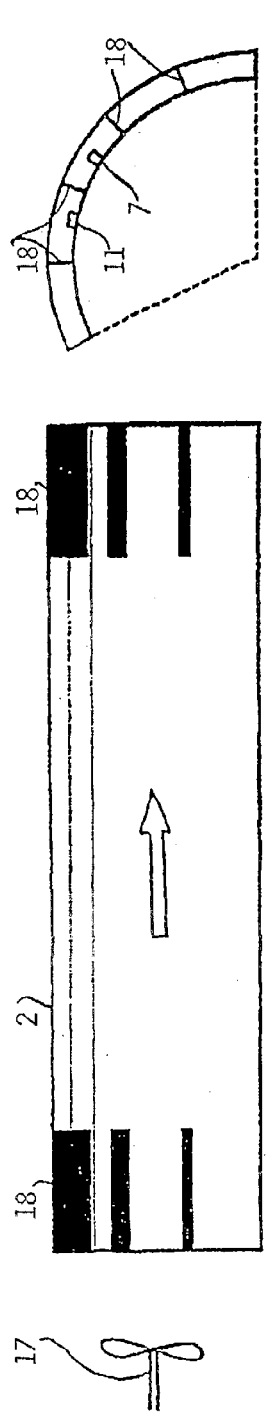
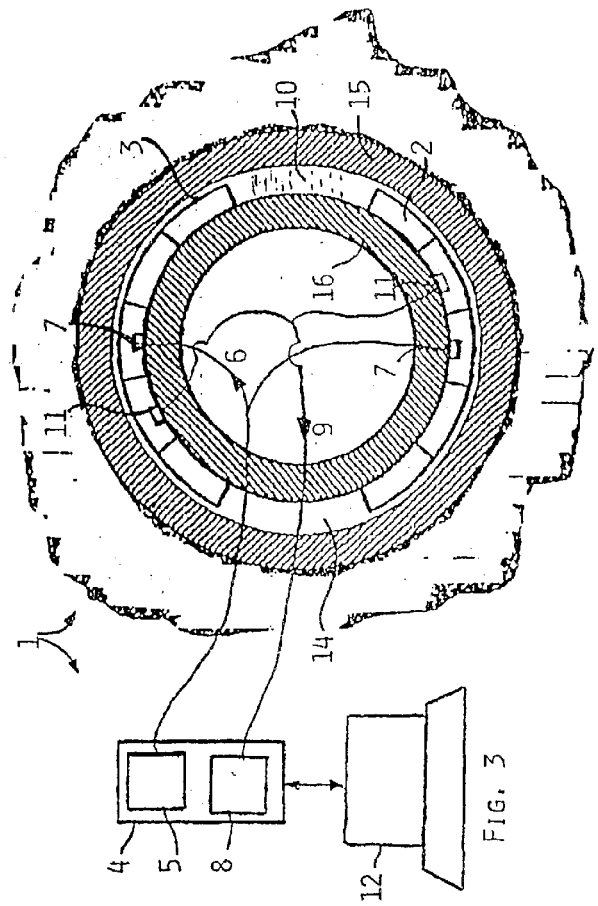
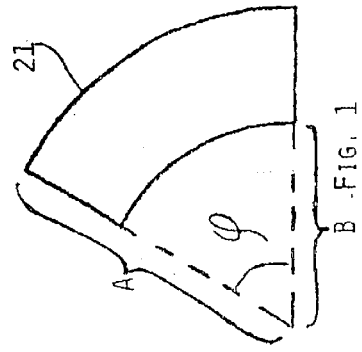
FIG. 1
FIG. 2
FIG. 3

METHOD FOR MEASURING PROPERTIES OF FLOWING FLUIDS, AND A METERING DEVICE AND A SENSOR USED FOR PERFORMING THIS METHOD

The invention relates to a meter and a sensor concept, and also to a method for measuring properties of a fluid flow. The meter comprises a sensor, an electronic unit, and a software package, in particular for the continuous measurement of the composition of a fluid flowing through a duct or channel. In this document in particular the use as a downhole meter for the measurement of the water fraction of the fluid being produced in an oil well is described. However, the invention may also be used for measuring other properties and values.

The sensor is based on using both the microwave resonance principle for the measurement of oil-continuous fluids (water drops and gas bubbles in oil, i.e. the oil is the continuous phase), and the measurement of conductivity for water-continuous fluids (oil drops and gas bubbles in water, i.e. the water is the continuous phase). The meter is intended for installation at a production zone inside an oil well.

The meter can also measure the fluid that is being produced from a specific zone. The measurement result can be used for controlling a valve that controls the production rate from the zone. Such equipment is especially useful in so-called smart wells, in which several zones produce into the same well. The in-flow from one zone is being mixed with the main flow (that has been produced from other zones and flows in a tube system) at the valve controlling that zone. The composition ought to be measured inside the well (down-hole) between the perforations in the casing or liner and the valve, while the fluid is flowing in the annulus, before it is being mixed with the main flow. Knowing the composition of the fluid being produced is important for the long-term optimization of the recovery from a zone.

There are a number of different meters on the market for the measurement of the water contents of oil. Some meters are based on the use of radioactive radiation, some are capacitive, and some are based on the use of microwaves. The radioactive sensors are problematic in many environments because of the health risks with such radiation, and the safety measures required. In downhole applications this would encounter a serious problem, particularly during the installation phase. In addition the accuracy is a problem because the radiation is mainly sensitive to differences in density, and the difference in density of oil and water is small or even zero. The capacitive sensors measure the permittivity (ref. chapt. 2 in Nyfors E., and P. Vainikainen, Industrial Microwave Sensors, Norwood, Mass.: ArtechHouse, 1989) of the fluid at frequencies that are much lower than those used by microwave sensors. They are therefore very sensitive to all kinds of contamination, as a thin layer of e.g. scale or wax has a large influence on the impedance of such sensors. They also require a relatively complicated mechanical structure including a dielectric protecting cover on the inside of the sensor, so that the electrodes do not come in direct contact with the fluid that is measured. Microwave sensors do not have these problems. A microwave sensor measures the permittivity of a fluid. Because the permittivity of water is much higher than that of most other substances, oil included, the permittivity of a fluid containing water is very sensitive to the water content.

Currently there are no sensors of any kind available on the market for the measurement of the water content of fluids neither in the annular space between two pipes, nor downhole in an oilwell.

The conditions that a meter for measuring operations downhole in the annulus of an oilwell has to face are difficult. These are the high pressure (typically up to 1000 Bar), the high temperature (typically up to 180° C.), the very limited space, the low electrical power available (because of the typically several km long supply cable), and the high required reliability because of no possibilities to service the meter once it has been installed with the completion of the oilwell. These conditions require a specially designed microwave sensor for the annulus. The sensor must also be designed so that a measurement principle can be used that requires an absolut minimum amount of electronics at the downhole location of the sensor because of the limited space, the limited power, and the requirement on reliability in combination with the high temperature. The measurement method should also be such that a minimum amount of information needs to be transferred to the surface, because of the low data handling capacity of a several kilometers long combined power/signal cable.

The resonant frequency of a microwave resonator sensor can be measured with basically two different methods (ref. Vainikainen, P., "Measurement electronics of industrial microwave resonator sensors", Thesis for the degree of Doctor of Technology, Helsinki University of Technology, Radio Laboratory, Report S 194, 1991).

The first involves measuring the frequency response of the resonator by performing a frequency sweep, with e.g. a VCO (voltage controlled oscillator). The resonant frequency is then usually derived by performing a curve fit. If this method would be used in a downhole application, either the whole frequency response, typically involving hundreds of measurement points, would have to be transferred to the surface for one measurement of the water content, or there would have to be a data processing capability in the downhole electronics. Transferring the frequency response to the surface is slow, and processing the data downhole would make the electronic unit much more complex and unreliable.

The second is the so-called FSA method (feedback self-oscillating amplifier), which is based on locking an oscillator to the resonant frequency of the sensor. The FSA method is fast and simple. The frequency only needs to be counted downhole and transferred to the surface as a single number for each measurement of the water content. The FSA method requires a pure frequency response in the sense that there should be no other resonance peaks near the one used, so that it can be assured that the electronics always locks to the right resonance peak.

This invented sensor is a microwave cavity resonator of a new design, in particular adapted for downhole use, e.g. in an oil/gas well. The advantages are that it is suitable for permanent installation in an annulus, the frequency response that makes it suitable for measurement with the FSA method, a simple structure, and probes that can also be used for measuring the conductivity of the fluid for determining the water content, when the fluid is water-continuous. With these features a minimum amount of electronics is required downhole, which allows for obtaining a good reliability also at the high temperatures encountered in the downhole environment. A minimum amount of data transmission is needed, which enables for fast measurements. All software for performing the necessary calculations of the water content can be located at the surface.

These advantages can be obtained by using the techniques, features and methods according to the claims stated below.

A more detailed description of some embodiments of the invention is given below and a preferred embodiment is in particular shown. The application as a permanent downhole meter for measuring the water content of the in-flow from a single zone in an oilwell is used as an example. The following figures are used in the description:

FIG. 1 The cross section of a semisectorial waveguide.

FIG. 2 The design of the downhole semisectorial cavity resonator sensor, shown by an longitudinal view and one cross section.

FIG. 3 The cross section of an oil well with two sensors of the above type mounted in the annulus in the well.

FIG. 4 The electric field intensity in the sensor of the TE modes with n & l ≦3, m=1 projected on a cylindrical folded out surface. The location of the probes are marked with crosses.

Figure 5:
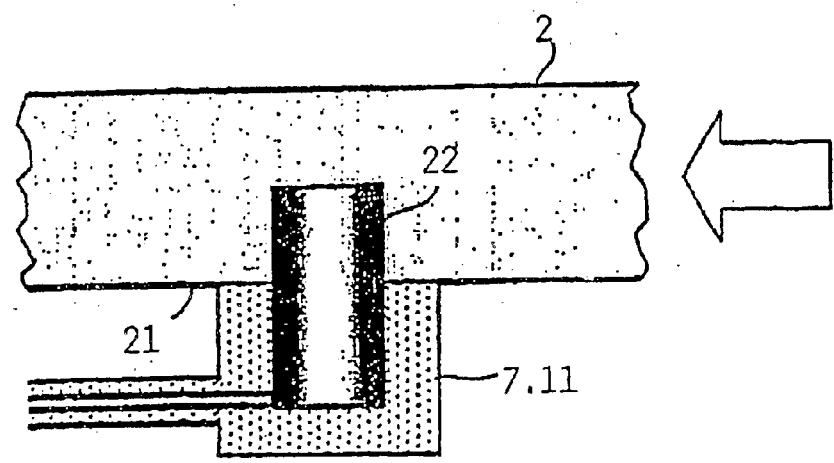

FIG. 5 The design of the probes seen in cross section.

Figure 6:
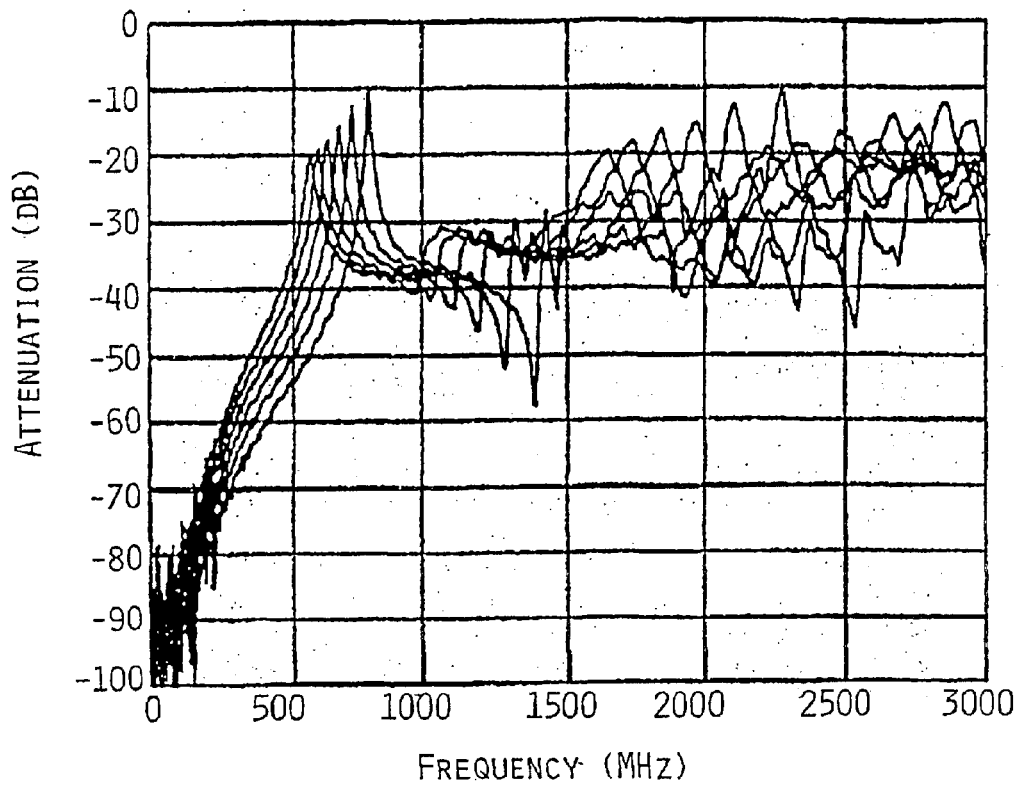

FIG. 6 The frequency response of the sensor as measured with a network analyzer. The salinity of the water is 3%. The water content varies stepwise from 0% to 25%.

Figure 7:
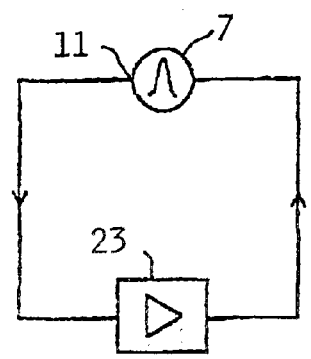

FIG. 7 The principle of the FSA method of measuring the resonant frequency.

In the figures the same reference numerals are used for identical or similar components and elements when found applicable. It should also be noted that the figures are drawings primarily depicting the principles and accordingly some practical details may be omitted even if required to implement the invention. Eventually it should be mentioned that the scale is not the same on each drawing, not even in different parts or different directions of one single drawing.

In FIG. 1 the main shape of a so-called semisectorial sensor 2 is shown as a cross section. The shape of a sensor 2 may thus be defined by the angle φ, the inner radius b and the outer radius a. The surrounding wall 21 of the sensor 2 is made up of a rigid and electric conducting material having a hollow design so that the fluid may pass freely through the "curved tube", perpendicularly to the paper plane. The number of semisectors which may be arranged within an annular space, e.g. between a production tube and a casing in an oil or gas well, will depend on the angle φ.

The length of the sensor 2 is shown on FIG. 2, which on left hand shows a view taken along the axis of the sensor and on right hand shows an end view of the sensor. Here it is assumed that end grids 18, also conducting, are arranged at both ends of the sensor 2. As it is seen, the medium portion of the sensor includes only one single chamber, while the end grids only are introduced at the end portions to screen off the cavity of the resonator from the surroundings.

In FIG. 3, there is shown as a preferred embodiment that two such sensors 2,3 are aranged as an integral unit within the annulus of a production tube, preferably downhole in an oil/gas well. Then also high frequency equipment may be included in the downhole unit, while all other equipment such as the electronic circuit 4 and possible computing or signal treating units (12) may be arranged at the surface.

FIG. 4 shows the field within the sensor for different wave modi. The x marks visible in the diagrams represent the location of the probes used in an PSA operation, as explained below.

In FIG. 5 an embodiment of a probe 7,11 is shown in more detail. Here a coaxial probe construction is assumed, but other conventional probe designs may be used as well.

On FIG. 6 the frequency response is shown as explained later in the specification, and in FIG. 7 the FSA method is shown in principle, as explained furhter down.

The invention is recognized by that when the permittivity of a fluid is measured for determining the composition, a microwave cavity resonator is used. The resonator is a semisectorial cavity resonator with end structures consisting of radial-axial plates or end grids 18, which allows the flow to pass through the sensor 2 unhindered. The probes are located so that coupling to the resonance modes in the vicinity of the used mode is eliminated, making the sensor well suited for the FSA method of measuring the resonant frequency. The same probes that are used for coupling the microwave signal to the sensor can also be used for measuring the conductivity of the fluid, in case of e.g. a water-continuous fluid consisting of oil, water, and gas. The software for calculating the composition may be located at a large distance, e.g. at the surface in the case of the application of measuring downhole in an oilwell, because of the small amount of data transfer needed. In front (upstreams) of the sensor there may be a mixer 17, of any conventional type, that assures that the fluid is well mixed in case the fluid has segregated while flowing in the annulus.

The pressure drop over this mixer, or some other part in the annulus creating drag, may also be measured and the flow speed derived from an empirically calibrated model. From the flow speed and the composition measurement, production rates of e.g. water and hydrocarbons can be calculated.

The calculation methods will be explained below:

When two material components (A and B), (liquid, gas, or solid particles), with different permittivity ($\epsilon_A$ and $\epsilon_B$) are mixed, the mixture has a permittivity $\epsilon_m$ that is dependent on the mixing ratio φ of the two components (ref. chapt. 2 in Nyfors E., and P. Vainikainen, Industrial Microwave Sensors, Norwood, Mass.: ArtechHouse, 1989). The mixing ratio is usually expressed as the total volume of one of the components relative to the volume of the mixture, e.g.

$$\phi_A = \frac{V_A}{V_A + V_B} \tag{1}$$

where $V_A$ is the volume of component A and $V_B$ is the volume of component B in a sample of volume $V_m=V_A+V_B$ of the mixture. If e.g. A is water and B is oil, $\phi_A$ is the water content of the mixture. In the case of the fluid produced in an oil well, B may in turn be a known mixture of oil and gas, and will therefore be generally called the hydrocarbon component. The way $\epsilon_m$ depends on φ depends on how the components mix with each other and is therefore specific for these components. As a model for this dependence a known model (ref. chapt. 2, 4 in Nyfors E., and P. Vainikainen, Industrial Microwave Sensors, Norwood, Mass.: ArtechHouse, 1989), may be used, or an empirical calibrated model. By using this model, φ can then be derived from a measured value of $\epsilon_m$.

For the measurement of $\epsilon_m$, a microwave resonator can be used as a sensor. Such a sensor has a resonant frequency that is dependent on the permittivity of the medium with which it is filled. If $f_0$ is the resonant frequency of the sensor, when it is empty, and $f_m$, when it is filled with the mixture, the permittivity is, as stated in Nyfors E., and P. Vainikainen, Industrial Microwave Sensors, Norwood, Mass.: ArtechHouse, 1989.

$$\varepsilon_m = \left(\frac{f_o}{f_m}\right)^2 \tag{2}$$

It is previously known that microwave resonators for the measurement of fluids can be made of cylindrical pipes with relatively open end grid structures that allow the fluid to flow through the sensor, but prevents the microwaves from escaping. Ref. e.g. U.S. Pat. No. 5,103,181 (Gaisford et al). The present invention comprises a new type of microwave cavity resonator sensor, shaped to fit into the annulus and with end grid structures. The cross section of the sensor is the part of a sector that is limited between two concentric circles. Such a shape will here be called a semisector (FIG. 1).

The new sensor is thus a semisectorial cavity resonator sensor. It should be emphasized that there may be used one, two or more than two such semisectorial elements within the annulus. Accordingly "semi" does not refer to the half of the cirumferial, but rather to any portion of the perimeter. The space not filled up with a waveguide may be used for cables, connectors, etc.

In hollow waveguides, i.e. electrically conducting pipes, microwaves can propagate in various wave modes called TE or TM wave modes (ref. chapt. 3 in Collin, R. E., Foundations for Microwave Engineering, New York: McGraw-Hill, 1966) having specific cut-off frequencies. Power can propagate on a specific mode only at frequencies above the cut-off frequency of that mode. The modes in semisectorial waveguides can be solved following the same procedure as for cylindrical waveguides. The modes are then called $TE_{vm}$ or $TM_{vm}$, and their cut-off frequencies are given by $$f_{c \cdot vm} = \frac{c \cdot P_{vm}}{2\pi a}, \quad (TM_{vm}) \quad (3)$$

$$f_{c \cdot vm} = \frac{c \cdot P'_{vm}}{2\pi a}, \quad (TE_{vm}) \quad (4)$$

where c is the speed of light in vacuum ($3 \times 10^8$ m/s), and a is the larger radius of the semisector (FIG. 1). The index $v$ is given by $$v = \frac{n\pi}{\phi_0} \quad (5)$$

where $\phi_0$ is the sector angle (FIG. 1), and n is an integer (n=0, 1, 2, . . . (TE), and n=1, 2, 3, . . . (TM)). $P_{vm}=k_c a$ is the m:th solution to the equation $$\frac{J_v(k_c a)}{J_v(k_c b)} \cdot \frac{Y_v(k_c b)}{Y_v(k_c a)} - 1 = 0 \quad (6)$$

where $J_v$ and $Y_v$ are Bessel functions of the first and second kind and order $v$, b is the smaller radius (FIG. 1) and $$k_c = \frac{2\pi f_c}{c} \quad (7)$$

$P'_m = k_c a$ is the m:th solution to the equation $$\frac{J'_v(k_c a)}{J'_v(k_c b)} \cdot \frac{Y'_v(k_c b)}{Y'_v(k_c a)} - 1 = 0 \quad (8)$$

where the apostrophe denotes the derivative with respect to the argument of the function. In the general case Eqs. (6) and (8) can only be solved numerically.

A microwave resonance mode in a semisectorial cavity resonator is based on a $TE_{vm}$ or $TM_{vm}$ waveguide mode. The resonator is a length L of the semisectorial waveguide bounded by end structures that provide an open or short circuit to the wave mode, so that the waves are reflected back and forth generating a standing wave pattern in the bounded waveguide section. The wave mode gets a third index l associated with the length L of the resonator. The resonant frequency of the various modes is then (ref. Nyfors E., and P. Vainikainen, Industrial Microwave Sensors, Norwood, Mass.: ArtechHouse, 1989, p 150).

$$f_{r, vml} = \frac{c}{2}\left[\left(\frac{x_{vm}}{\pi a}\right)^2 + \left(\frac{1}{L}\right)^2\right]^{\frac{1}{2}} \quad (9)$$

where $x_{vm}$ denotes $P_{vm}$ or $P'_{vm}$. The invention is a resonator with short-circuiting ends and can therefore support $TM_{vml}$ modes with index l=0,1,2, . . . and $TE_{vml}$ modes with l=1,2,3, . . . .

In the invention a microwave semisectorial cavity resonator sensor has been designed for measuring the water content of the fluid produced by an oilwell, while the fluid is flowing in the annulus. An example of the resonator is shown in FIG. 2, and FIG. 3 shows a cross section of the oil well with two such sensors mounted on the outside of the tubing. The sensor has a small clearing to the casing, which is necessary when the tubing (incl. sensors et.c.) is slided in place during completion of the oilwell. Two sensors can be used as shown in FIG. 3 to improve the reliability by providing redundancy, or to improve the sampling in case of segregation. Two sections of the circumference of the tubing have been left free in FIG. 3 to allow space for cables etc. bound for other production zones deeper in the well to pass.

The embodiment shown in FIG. 2 may be used for different well sizes, however, the sensor shown was designed for a well with a 4" tubing in a 7" liner (a 7" casing is called a liner). Table 1 shows the resonant frequency of the 10 modes with the lowest resonant frequency, and FIG. 4 shows a qualitative picture of the electric field intensity of the TE modes with n & l≦3, m=1 projected on a cylindrical surface. The mode with the lowest resonant frequency ($TE_{vll}$, n=1) was chosen for the measurement purposes, because it is the most practical choice, especially when the FSA method is used.

TABLE 1

The resonant frequency of the 10 modes with the lowest resonant frequency in a semisectorial microwave cavity resonator sensor with the dimensions: a = 72 mm, b = 62 mm, $\phi_0$ = 128.3°, and L = 225 mm. v was given by (5), $P'_{v1}$ by (8), and $f_r$ by (9). Note that the $P_{vm}$ values calculated from (6) show that all TM modes in the resonator have higher resonant frequencies than those shown in the table.

| Mode | n | v | $P'_{v1}$ | $f_r$ |
| --- | --- | --- | --- | --- |
| $TE_{n11}$ | 1 | 1.403 | 1.509 | 1.202 |
| $TE_{n12}$ | 1 | 1.403 | 1.509 | 1.667 |
| $TE_{n11}$ | 2 | 2.806 | 3.018 | 2.110 |
| $TE_{n13}$ | 1 | 1.403 | 1.509 | 2.236 |
| $TE_{n12}$ | 2 | 2.806 | 3.018 | 2.405 |
| $TE_{n13}$ | 2 | 2.806 | 3.018 | 2.829 |
| $TE_{v14}$ | 1 | 1.403 | 1.509 | 2.848 |
| $TE_{n11}$ | 3 | 4.209 | 4.527 | 3.075 |
| $TE_{v12}$ | 3 | 4.209 | 4.527 | 3.285 |
| $TE_{n14}$ | 2 | 2.806 | 3.018 | 3.334 |

When measuring the resonant frequency of a resonator sensor with the FSA method, two coupling probes are needed. Because the used mode has a purely radial electric field, coupling probes of the electric type (ref. Nyfors E., and P. Vainikainen, Industrial Microwave Sensors, Norwood, Mass.: ArtechHouse, 1989) located radially is the natural choice. The basic design used in the invention is shown in FIG. 5. In the realized design the probes are mounted on the concave cylindrical surface in the locations indicated by the crosses in FIG. 4. One has equal distance to the broad ends and is displaced ⅓ of the distance from the centre towards one short end, and the other one has equal distance to the short ends and is displaced ⅓ of the distance from the centre towards one broad end. In these positions at least one of the probes is always in a null of a mode with at least one even numbered index (n or l), or at least one index equal to 3, so avoiding coupling to these modes. This is also clearly seen in FIG. 4 from the fact that maximum one of the crosses is visible, except for the used mode. With the probes mounted in the indicated positions, a frequency response is achieved that is well suited for the FSA method. FIG. 6 shows the frequency response of the sensor as measured with a network analyzer, when the sensor is filled with various mixtures of oil and water of various water content. It can be concluded that there are no confusing resonance peaks in the vicinity of the used peak. The sensor is therefore well suited for measurement with the FSA method.

The end grid structure of the sensor consisting of radial/axial plates is shown in FIGS. 2 and 3. The plates basically divide the semisectorial waveguide into 5 smaller semisectorial waveguides. Because of the smaller sector angle they will have a higher cut-off frequency. In the shown design the cut-off frequency of the grids is 5 GHz in air. Because this is higher than the used resonant frequency of 1.2 GHz (Table 1), the microwaves cannot escape through the end grids. Because the below-cut-off attenuation is finite, the end grids need to have a finite length. The shown 50 mm has been found to be enough. When the sensor is filled with the measured fluid, both the resonant frequency and the cut-off frequency of the grids will change according to equation (2), but the ratio will be constant. Therefore the grids will be tight under all conditions. The grids create almost no blockage to the flow, which makes this sensor ideal for measuring a flowing fluid.

The FSA method was described in detail in Norwegian patent application No. 98.2538, and will be described only briefly here. The principle of the FSA method is shown in FIG. 7. The output of an amplifier 23 is coupled to one probe 7 of a resonator sensor. The signal is received with the other probe 11 and fed back to the input of the amplifier 23. When the insertion loss in the sensor is lower than the gain in the amplifier, there is net gain in the circuit, which leads to oscillation. If the amplifer has a gain that is falling with frequency, the used resonance is the lowest one, and there are no other resonances near the used one, i.e. oscillation is possible only at the right resonance peak. In addition to the gain condition there is, however, also a phase condition for oscillation: The total phase change experienced by the signal during one revolution in the circuit must be $$\Delta\phi = n \cdot 360° \quad (10)$$

where n is an integer. This means that the circuit generally does not oscillate exactly on the resonant frequency, but on the nearest frequency where the phase condition is fulfilled. When the composition changes so that the resonant frequency changes, the oscillation jumps from one frequency (n) to the next (n±1) in steps. Because the phase change is dominated by the phase change in the cables, the size of the step depends primarily on the length of the cables:

$$\Delta f = \frac{(n+1)c}{d\sqrt{\varepsilon_c}} - \frac{n \cdot c}{d\sqrt{\varepsilon_c}} = \frac{c}{d\sqrt{\varepsilon_c}} \quad (11)$$

where d is the total length of the cables and $\varepsilon_c$ is the permittivity of the insulating material in the cables. Because of the phase change in both the sensor and the electronics the real step is slightly smaller. In practice the discrete nature of the FSA method means that the resolution of the resonant frequency measurement is limited primarily by the length of the cables. If d=10 m and $\varepsilon_c$=9, →Δf=10 MHz. Because the sensitivity of the sensor is roughly 10 MHz/%(water), the resolution is roughly 1%(water), which is sufficient for the downhole application.

The sensor has been tested in a test loop filled with crude oil and water with various salinity (S=0 . . . 15%). The resonant frequency was measured both with a network analyzer and an FSA electronics that was built to fit into a housing with an inner diameter of 19 mm, and to be used downhole. The results were very good. The difference in the resonant frequency measured with the network analyzer and that measured with the FSA downhole electronics was in accordance with equation 11. The sensor worked well through the whole oil-continuous range (up to 76%(water) in this experiment) The difference between one curve and the next in this diagram corresponds to approx. 5%. In the water-continuous range the conductivity of the fluid was measured by measuring the load resistance of one of the probes. The results show that the measured load resistance can be calibrated against the water content, when the conductivity (salinity and temperature) of the water is known. Thereby the same sensor can be used also with water-continuous fluids (usually at the end of the life of an oilwell) by adding a simple electronic circuit that measures the load resistance of one of the probes.

A sensor has been described that is based on a microwave semisectorial cavity resonator. The end grid structure of the sensor creates no blockage to a flowing fluid, and the sensor fits into the annulus of an oilwell. Because of the location of the probes the sensor is well suited for measurement using FSA electronics, which has been built to fit into a housing that also fits into the annulus. Because of the design of the probes they can also be used for measuring the composition in water-continuous fluids based on measuring the load resistance. The sensor is therefore suitable for measuring the composition of the inflow from a production zone in a smart well.

The invention may be modified in many manners. More than one sectorial cylinder may be integrated in each curved unit, or with other words each sensor 2,3 may comprise not only one single but two or several parallel cavity resonators, each with its own probes. Such parallel resonators 2,3 may be separated by common partition walls as opposite sides of one single wall may be used in each adjacent resonator. Each resonator must be provided with separate probes. However, the probes must not necessarily have the design as shown in FIG. 5. Instead the probes may have any suitable design determined by skilled persons according to given requirements.

The complete meter may comprise one single downhole unit in which one single or more than one sensor are arranged. This downhole unit may then also include necessary cabeling and high frequency somponents, converters and interfaces, so that the unit may be deployed in one single operation.

If many small dimension sensors are arranged along the perimeter, a more or less geometric approach is feasible as some of the sensors then will have a flow of nearly pure water, while other of the sensors will have a flow of nearly pure oil, due to segregation. The principle then will be to count the number of sensors with mainly oil and the number of sensors containing mainly water. The accuracy of the result will then increase with the number of sensors. A mixer at the input then may be omitted, and the degree of segregation may also be determined.

Still another approach is to use only one probe in each sensor and then measure the reflected energy. Then an inverted pike (downward directed response) will be registered on the resonance diagram. The method used with only one probe then will be the frequency response method and not the FSA method, which in other cases is deemed to be the most advantageous, however, not the only feasible method.

What is claimed is:

1. A flow meter for continuous measuring properties of at least one fraction included in a flowing fluid composition comprising at least two different components flowing through a duct or channel which meter (1) comprises at least one sensor (2,3) designed as waveguide through which the fluid composition (10) flows, at least one electronic unit (A) comprising a transmitting means (5) adapted to transmit an electric signal (6) into the fluid composition (10)

at least one receiving means (8) adapted signal (9) by means of a receiving probe (11) the sensor (2,3), and at least one signal processor (12) adapted to deduce values (13) specific to the properties of the fluid from the received signal (9), characterised in that the sensor(s) (2,3) are in the shape of a resonator(s) and are designed to fit into an annular space (14) between one external tube (15) and an internal core (16) arranged therein, so that at least a portion of the fluid composition (10) flows through the sensor (2,3), and that the sensor(s) comprises at least one cylindrical sector made of thin walled, electrically conducting material and with a cross section shaped as a semi-sector (2,3) having dimensions which preferably allows one or more sensors to be arranged adjacent to each other or separated from each other within the annular space (14).

2. Flow meter according to claim 1, characterised in that a mixer (17) is arranged upstream of each sector shaped sensor.

3. Flow meter according to claim 1, characterised in that each sensor (2,3) comprises at least one semi-sectorial cavity resonator.

4. Flow meter according to claim 1, characterised in that each sensor (2,3) is provided with an end grid (18) at each of its ends (19), allowing the fluid to flow unhindered, while stopping the microwaves.

5. Flow meter according to claim 1, characterised in that each sensor is provided with at least one internal microwave probe (22) adapted to transmit and/or receive microwave energy into/from each cavity resonator (2,3), said microwave probe(s) (22) being located at a null-point for a specific oscillating mode, to avoid coupling to specific predetermined modes.

6. Flow meter according to claim 1, wherein the electronic unit (4) comprises an oscillator which is adapted to be phase locked to a resonant frequency of the sensor (2,3) in a so-called FSA-method (feedback self-oscillating amplification) and wherein the frequency is determined downhole, while the result is transferred to the surface as a number representing each measurement of the desired property(ies).

7. Flow meter according to claim 6, for measurement on a fluid composition comprising water and hydrocarbons, comprising measuring means for measuring the pressure drop over the meter (1) or some of the components of the fluid, means to derive the flow speed from this measurement using an empirically calibrated model, and means to combine these results with the properties found by the microwave measurement to give separate production rates of water and hydrocarbons.

8. A sensor adapted for downhole use, in particular in a subsurface production well, characterised in that a resonator sensor(s) (2,3) is designed to fit into an annular space (14) between one external tube (15) and an internal core (16) arranged therein, so that at least a portion of the fluid composition (10) flows through the sensor (2,3), and that the sensor(s) comprises at least one cylindrical sector made of a thin walled, electrically conducting material and with a cross section shaped as a semi-sector (2,3) having dimensions which preferably allows one or more sensors to be arranged adjacent to each other or separated from each other within the annular space (14).

9. A sensor according to claim 8, comprising at least one semi-sectorial cavity resonator.

* * * * *